United States Patent
Hay et al.

(10) Patent No.: US 8,263,012 B2
(45) Date of Patent: Sep. 11, 2012

(54) PHOTOCATALYST PROTECTION

(75) Inventors: Stephen O Hay, South Windsor, CT (US); Susan D. Brandes, South Windsor, CT (US); Norberto O. Lemcoff, Simsbury, CT (US); Timothy N. Obee, South Windsor, CT (US); Wayde R. Schmidt, Pomfret Center, CT (US)

(73) Assignee: Carrier Corporation, Syracuse, NY (US)

( * ) Notice: Subject to any disclaimer, the term of this patent is extended or adjusted under 35 U.S.C. 154(b) by 253 days.

(21) Appl. No.: 12/759,009

(22) Filed: Apr. 13, 2010

(65) Prior Publication Data

US 2010/0196223 A1 Aug. 5, 2010

Related U.S. Application Data

(62) Division of application No. 11/011,730, filed on Dec. 14, 2004, now Pat. No. 7,740,810.

(51) Int. Cl.
*B01J 19/08* (2006.01)
(52) U.S. Cl. ............... 422/186.04; 422/186.3; 422/121
(58) Field of Classification Search ............ 422/186.04, 422/186.3, 121
See application file for complete search history.

(56) References Cited

U.S. PATENT DOCUMENTS

| | | | |
|---|---|---|---|
| 4,990,311 A | 2/1991 | Hirai | |
| 5,933,702 A | 8/1999 | Goswami | |
| 5,993,738 A | 11/1999 | Goswani | |
| 6,022,456 A * | 2/2000 | Manning | 204/176 |
| 6,149,717 A | 11/2000 | Satyapal | |
| 6,238,629 B1 | 5/2001 | Barankova | |
| 6,358,374 B1 | 3/2002 | Obee et al. | |
| 6,508,982 B1 | 1/2003 | Shoji | |
| 6,607,702 B1 | 8/2003 | Kang et al. | |
| 6,680,033 B2 | 1/2004 | Ishii | |
| 6,866,828 B2 | 3/2005 | Segawa et al. | |
| 6,955,708 B1 | 10/2005 | Julos et al. | |
| 7,063,733 B2 | 6/2006 | Mori et al. | |
| 2003/0089237 A1 | 5/2003 | Jagtoyen et al. | |
| 2004/0007000 A1 | 1/2004 | Takeda et al. | |
| 2004/0065078 A1 | 4/2004 | Schafer-Sindlinger et al. | |
| 2004/0175318 A1 | 9/2004 | Segawa et al. | |

FOREIGN PATENT DOCUMENTS

| | | |
|---|---|---|
| CA | 2192048 | 1/2004 |
| CN | 2655913 | 11/2004 |
| DE | 10211810 | 10/2003 |
| EP | 02826531 | 3/1998 |

(Continued)

OTHER PUBLICATIONS

Supplemental European Search Report and dated Aug. 9, 2011.
International Search Report and Written Opinion mailed on Mar. 5, 2007 for PCT/US05/42708.
Extended European Search Report mailed Mar. 9, 2009 for EP05849872.

(Continued)

*Primary Examiner* — Kishor Mayekar
(74) *Attorney, Agent, or Firm* — Carlson, Gaskey & Olds, P.C.

(57) ABSTRACT

A gas treatment system for treating a gas stream containing contaminants includes first and second gas treatment members in fluid communication with each other. Each of the first and second gas treatment members is selectively controllable between an on and an off condition. A third gas treatment member is in fluid communication with the first and second gas treatment members, and the third gas treatment member selectively retains or releases the contaminants based upon the on or off condition of at least one of the first or second gas treatment members.

15 Claims, 4 Drawing Sheets

FOREIGN PATENT DOCUMENTS

| | | |
|---|---|---|
| EP | 1014006 | 6/2000 |
| EP | 1258281 | 11/2002 |
| EP | 1348448 | 10/2003 |
| EP | 1405663 | 4/2004 |
| EP | 1600201 | 11/2005 |
| EP | 1671659 | 6/2006 |
| JP | 2000102596 | 4/2000 |
| WO | 2005037335 | 4/2005 |

OTHER PUBLICATIONS

Junhong Chen and Jane H. Davidson, "Chemical Vapor Deposition of Silicon Dioxide by Direct-Current Corona Discharges in Dry Air Containing Octamethylcyclothetrasiloxane Vapor: Measurement of the Deposition Rate", Plasma Chemistry and Plasma Processing, vol. 24, No. 2, Jun. 2004, Plenum Publishing Corporation, pp. 169-188.
China Patent Office Action Dated Feb. 20, 2009.

* cited by examiner

PHOTOCATALYST PROTECTION

CROSS-REFERENCE TO RELATED APPLICATIONS

The present application is a Divisional Application which claims priority to application Ser. No. 11/011,730 now U.S. Pat. No. 7,740,810 filed Dec. 14, 2004.

BACKGROUND OF THE INVENTION

This invention relates to air treatment modules and, more particularly, to protecting a photocatalyst in the air treatment module using a corona discharge device to remove contaminants from the air handling air stream.

Air treatment modules are commonly used in automotive, commercial and residential heating, ventilating, and air conditioning (HVAC) systems to move and purify air. Typically, an air stream flowing through the air treatment module includes trace amounts of contaminants such as biospecies, dust, particles, odors, carbon monoxide, ozone, semi-volatile organic compounds (SVOCs), volatile organic compounds (VOCs) such as formaldehyde, acetaldehyde, toluene, propanol, butene, and silicon-containing VOCs.

Typically, a filter and a photocatalyst are used to purify the air stream by removing and/or destroying the contaminants. A typical filter includes a filter media that physically separates contaminants from the air stream. A typical photocatalyst includes a titanium dioxide coated monolith, such as a honeycomb, and an ultraviolet light source. The titanium dioxide operates as a photocatalyst to destroy contaminants when illuminated by ultraviolet light. Photons of the ultraviolet light are absorbed by the titanium dioxide, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When contaminants in the air stream flow through the honeycomb and are adsorbed onto the titanium dioxide coating, the hydroxyl radicals attack and oxidize the contaminants to water, carbon dioxide, and other substances. The ultraviolet light also kills the biospecies in the airflow that are irradiated.

Disadvantageously, typical air treatment module filters have a finite contaminant capacity. Once the contaminant capacity is reached, the filter does not physically separate additional contaminants from the air stream. Contaminants in the air stream may then flow through the filter and become oxidized by the photocatalyst. This is particularly troublesome when the photocatalyst oxidizes silicon-containing VOCs or SVOCs to form a silicon-based glass on the photocatalyst surface. The silicon-based glass may insulate the titanium dioxide from the passing air stream, thereby passivating the titanium dioxide. In severe instances, much of the catalytic activity of the photocatalyst may be lost within two weeks of reaching the contaminant capacity of the filter. To prevent photocatalyst passivation, the filter may be replaced before reaching the contaminant capacity or additional filters may be utilized to physically separate a greater amount of the contaminants, however, the maintenance required to replace a filter in short time intervals or continually monitor a filter may be expensive and inconvenient.

Accordingly, an air treatment module that more effectively protects the photocatalyst from passivating contaminants is needed.

SUMMARY OF THE INVENTION

A gas treatment system for treating a gas stream containing contaminants includes first and second gas treatment members in fluid communication with each other. Each of the first and second gas treatment members is selectively controllable between an on and an off condition. A third gas treatment member is in fluid communication with the first and second gas treatment members, and the third gas treatment member selectively retains or releases the contaminants based upon the on or off condition of at least one of the first or second gas treatment members.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
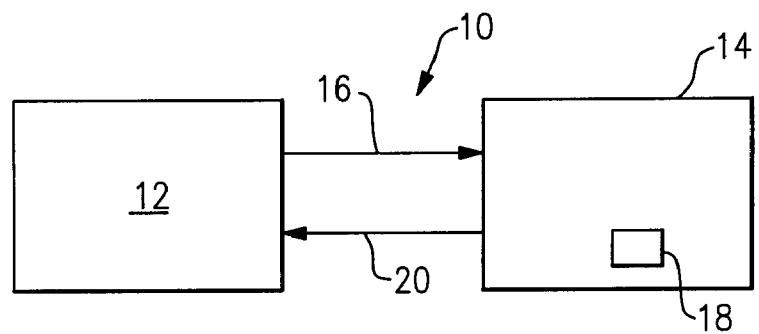
FIG. 1 is a HVAC system including an air treatment module.

FIG. 1 illustrates a residential, commercial, vehicular, or other structure 10 including an interior space 12, such as a room, office or vehicle cabin. An HVAC system 14 heats or cools the interior space 12. Air in the interior space 12 is drawn into the HVAC system 14 through an inlet path 16. The HVAC system 14 changes the temperature and purifies the air drawn using an air treatment module 18. The purified, temperature-changed air is then returned to the interior space 12 through an outlet path 20.

Figure 2:
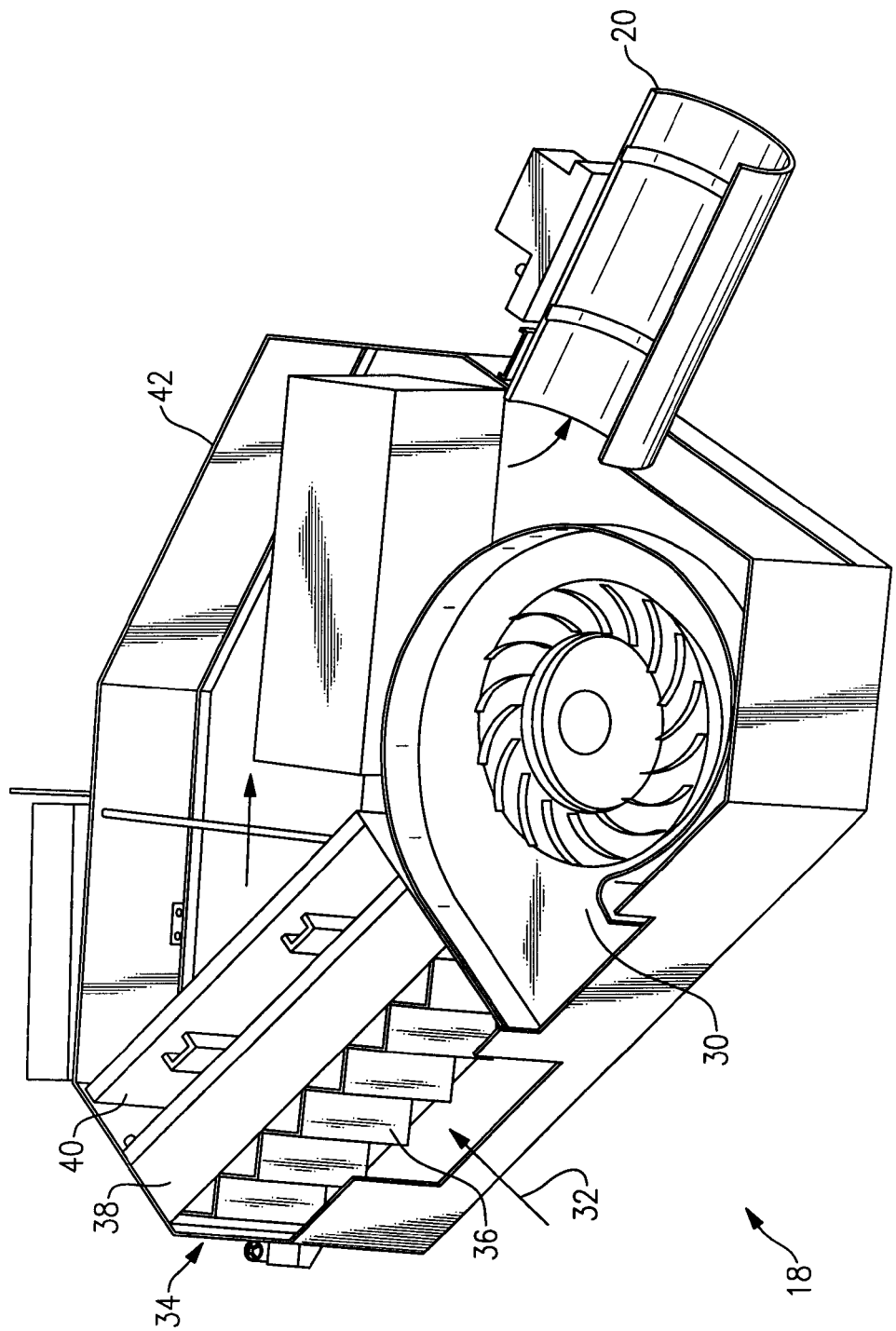
FIG. 2 is a perspective view of an example air treatment module.

FIG. 2 illustrates a perspective view of an example air treatment module 18. The air treatment module 18 includes a compressor 30 for drawing and returning the air. Air drawn from the interior space 12 flows in an air stream 32 into a filter cabinet 34, which forms an air flow path through the air treatment module 18. The filter cabinet 34 encloses a filter 36, plasma device 38, and photocatalyst 40 that cooperate to purify the air stream 32. The air stream 32 continues through the filter cabinet to the coils 42. The coils 42 heat or cool the air stream 32, depending on the desired interior space 12 temperature. After being heated or cooled, the compressor 30 returns the air stream 32 to the interior space 12 through the outlet path 20. It is to be understood that the air treatment module 18 shown is only one example and that the invention is not limited to such a configuration.

Figure 3:
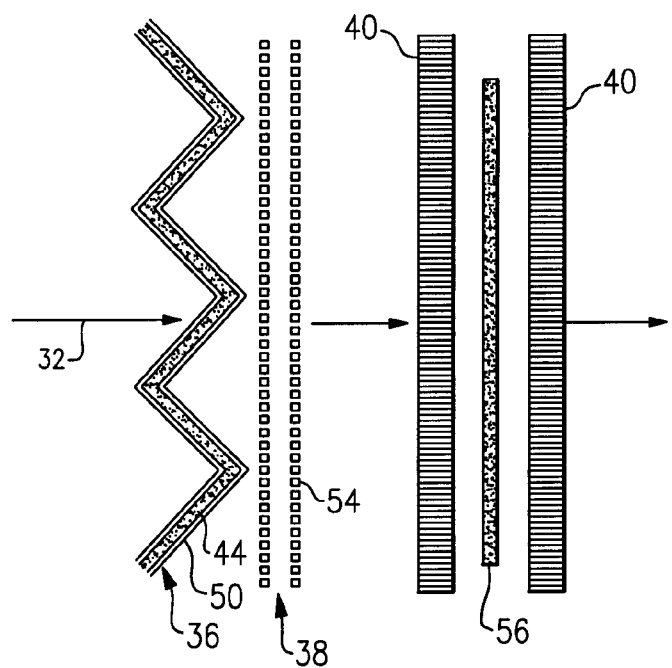
FIG. 3 is a schematic view of an example filter, plasma device, and photocatalyst.

FIG. 3 illustrates a schematic view of an example filter 36, plasma device 38, and photocatalyst 40. The filter 36 receives the air stream 32 and adsorbs contaminants from the air stream 32. The filter 36 includes a known activated carbon filter media held between layers of a fibrous mesh 44. In one example, the known activated carbon is modified, impregnated, or pore-controlled. As is known, a modifier such as potassium permanganate or other modifier may be impregnated in the activated carbon to modify the adsorptive properties of the activated carbon. The pore volume of the activated carbon may also be controlled within a desired range to modify the adsorptive properties. These features may provide the advantage of designing the filter 36 to preferentially adsorb certain contaminants, such as formaldehyde, acetaldehyde, toluene, propanol, butene, silicon-containing VOCs, or other VOCs.

In another example, the filter 36 may additionally utilize a zeolite and/or other type of filter media mixed with the activated carbon between the layers of fibrous mesh 44 to obtain preferential adsorption of certain contaminants. Alternatively, the activated carbon filter media may be integrated with the fibrous mesh 44 by coating the activated carbon onto fibers that make the fibrous mesh 44.

Figure 4:
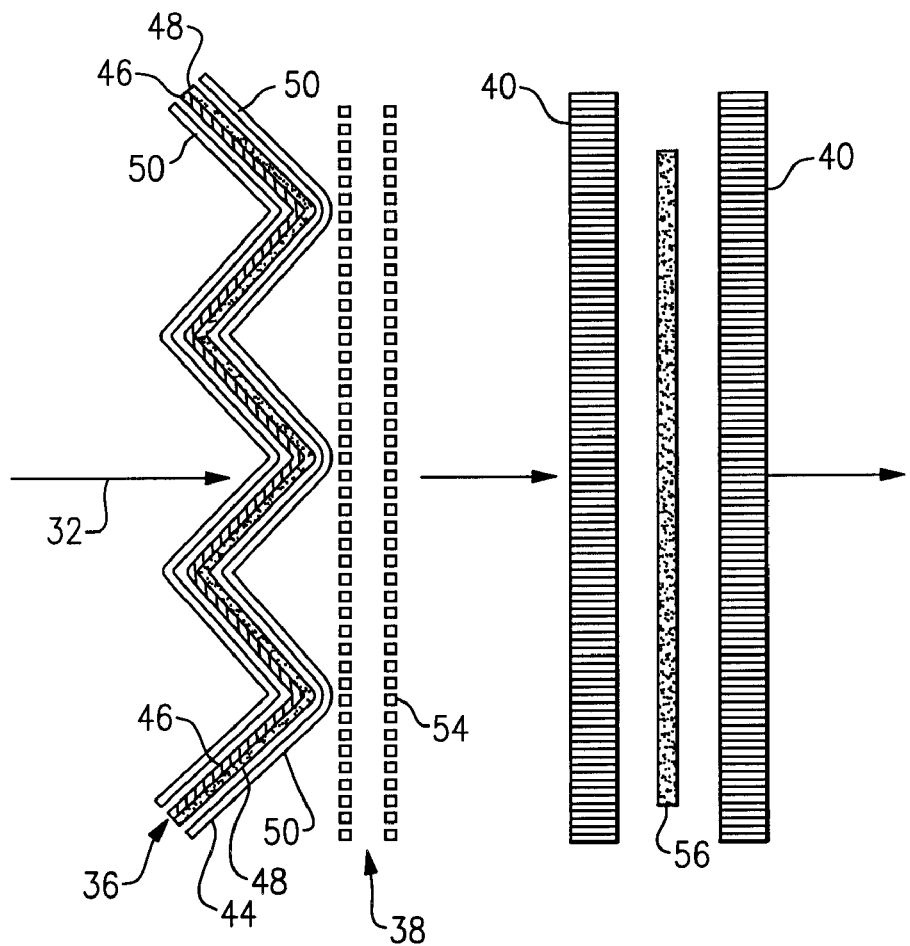
FIG. 4 is a schematic view another example of the filter of FIG. 3.

In another example, the activated carbon filter media is provided in a first layer 46 and the zeolite media and/or other filter media may be provided in an adjacent second layer 48, as illustrated in FIG. 4.

A heating element 50, which is discussed in more detail below, surrounds the filter 36 and is selectively operable between and on and an off condition.

In one example, the plasma device 40 is located generally downstream from the filter 36 and is selectively operable between an on and an off condition. Preferably the plasma device 38 is a corona discharge device that generates a plasma glow discharge. Even more preferably, the plasma device 38 includes a biased electrode 54, such as a wire cathode.

The photocatalyst 40 is, in one example, located downstream from the plasma device 38. Preferably the photocatalyst 40 is a titanium dioxide coated monolith, such as a honeycomb, that operates as a photocatalyst to destroy contaminants when illuminated with an ultraviolet (UV) light 56. It is to be understood that photocatalyst materials other than titanium dioxide and configurations other than shown (for example, integrating the photocatalyst 40 with the filter 36 in a single unitary fibrous or honeycomb structure) may be utilized.

The UV light 56 is selectively operable between an on condition in which the photocatalyst 40 operates to destroy contaminants, and an off condition in which the photocatalyst 40 is inoperable. In one example, the UV light 56 illuminates the photocatalyst 40 with UV-C range wavelengths, however, other UV wavelength ranges may be utilized depending on the type of photocatalyst and/or air purifying needs of the air treatment module 18.

Operationally, the exemplary air treatment module 18 functions in two different modes. In the first mode, the air treatment module 18 functions primarily to move air from and return air to the interior space 12 and to purify the air. In the first mode, the heating element 50 is selectively turned off, the plasma device 38 is selectively turned off, and the UV light 56 is selectively turned on. Thus, the filter 36 captures, traps, and adsorbs certain contaminants from the air stream 32, such as VOCs and SVOCs, and the photocatalyst 40 operates to destroy other contaminants that pass through the filter 36. The heating element 50 and plasma device 38 do not function in the first mode, however, in other examples it may be advantageous to simultaneously operate the heating element 50 and plasma device 38 with the functions of filtering and moving the air.

In the second mode, the air treatment module 18 functions primarily to regenerate the filter 36. That is, the activated carbon or other adsorbent filter media is conditioned to desorb the previously adsorbed contaminants. The air stream 32 is shut off such that there is essentially zero air flow in the filter cabinet 34. The heating element 50 is selectively turned on and heats the filter 36 to approximately 100° C., although other heating temperatures or heating profiles may also be utilized. The filter 36 desorbs and releases the contaminants previously adsorbed. The plasma device 38 is selectively turned on and generates a plasma, and the UV light 56 is preferably turned off to prevent the photocatalyst 40 from oxidizing the released contaminants.

The filter cabinet 34 holds the released contaminants and acts essentially as a reactor vessel for the plasma device 38. The released contaminants, such as VOCs, SVOCs, or other contaminants that the filter 36 was designed to adsorb/release, contact the plasma generated by the plasma device 38. The plasma chemically transforms the contaminants into solid contaminant products and deposits the solid contaminant products onto a receiving portion, the biased electrode 54. Once deposited, the essentially immobile and inert solid contaminant products are unlikely to damage the photocatalyst 40. In one example, the plasma deposits the solid contaminant products onto a wire cathode. After a predetermined number of deposit cycles, the wire cathode is removed from the plasma device 38 and discarded or cleaned.

While in the second mode, the heating element 50 and plasma device 38 operate for a selected predetermined amount of time. Preferably, the time is adequate to i) release most of the contaminants from the filter 36, and thus regenerate the filter 36 and ii) transform the contaminants to solid contaminant products. The time required will vary with temperature, size and type of filter media, size of the filter cabinet 34, and the size and type of plasma device 38 used.

Preferably, the UV light 56 remains off when switching from the second mode to the first mode to protect the photocatalyst 40 from any remaining contaminants that have not been transformed to solid contaminant products. The air stream 32 flows through the filter cabinet 34 for a selected predetermined amount of time to purge the remaining released contaminants before turning on the UV light 56 to operate the photocatalyst 40.

In another example, the contaminant products include organic silicon compounds, such as silicon-containing VOCs and silicon-containing SVOCs. The filter 36 releases the organic silicon compounds upon heating and the plasma generated by the plasma device 38 chemically transforms the organic silicon compounds into silicon dioxide or other silicon-based glass. The plasma deposits the silicon dioxide or other silicon-based glass on the biased electrode 54.

In another example, the filter 36 includes a single pleated layer with a pleating factor of about 8 and about 100 g of activated carbon filter media. The filter 36 adsorbs approximately 90% of the organic silicon compounds in the incoming air stream 32 and takes approximately twelve hours to reach full capacity in first mode operation. Near the twelve hour time, the air treatment module 18 utilizes, for example, a controller to automatically switch into the second mode and regenerate the filter 36. Alternatively or in addition to the controller, an operator may control the switching between modes.

Figure 5:
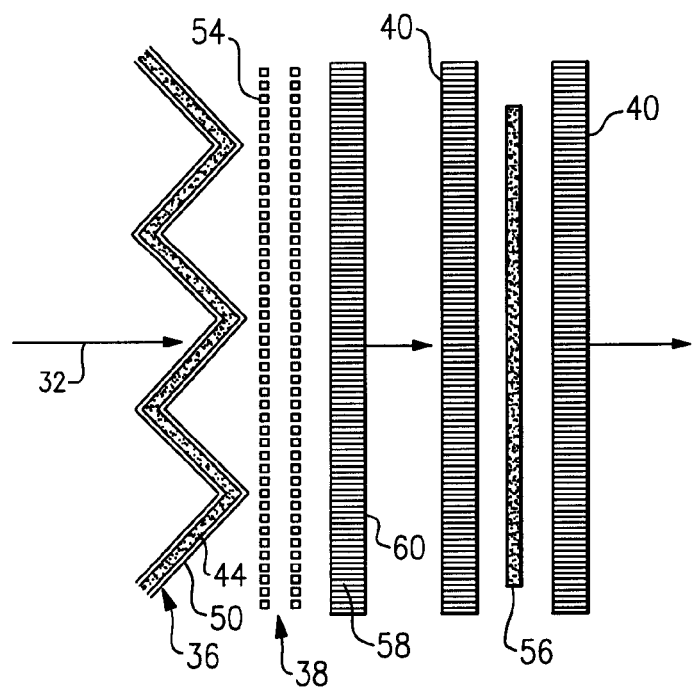
FIG. 5 is a schematic view an example air treatment module that includes an ozone-destroying material.

In another example shown in FIG. 5, an ozone-destroying material 58, such as a known metal oxide catalyst, is included between the plasma device 38 and the photocatalyst 40. The ozone-destroying material 58 may be disposed on a honeycomb structure 60, for example, and receives ozone from the plasma device 38 before switching the UV light 56 on. The ozone-destroying material 58 adsorbs ozone onto the surface and decomposes the ozone. This feature may provide the advantage of exposing the photocatalyst 40 to less ozone, which may contribute to photocatalyst 40 passivation. It is to be understood that the ozone-destroying material 58 may alternatively be positioned in other locations in the filter cabinet 34 than shown.

Figure 6:
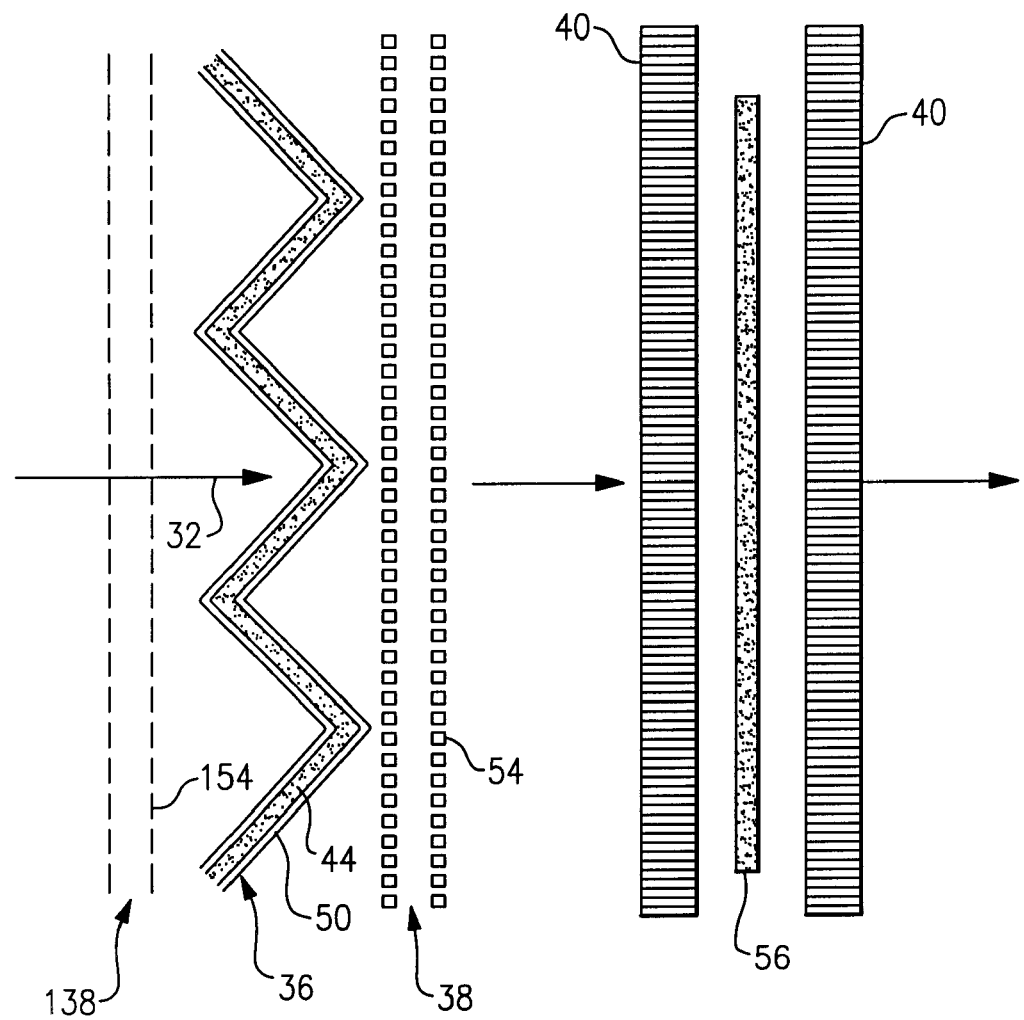
FIG. 6 is a schematic view of another air treatment module configuration that includes a second plasma device.

FIG. 6 illustrates a schematic view of another air treatment module 18 configuration including a second plasma device 138 surrounding the filter 36. The second plasma device 138 includes a biased electrode 154 and operates similarly to and in conjunction with the plasma device 38 to chemically transform released contaminants into solid contaminant products. Utilizing the second plasma device 138 may provide the benefit of shorter times to fully chemically transform the contaminants released from the filter 36 or greater efficiency in transforming the released contaminants. Likewise, a multitude of additional plasma devices may be used.

Although a preferred embodiment of this invention has been disclosed, a worker of ordinary skill in this art would recognize that certain modifications would come within the scope of this invention. For that reason, the following claims should be studied to determine the true scope and content of this invention.

We claim:

1. A gas treatment system for treating a gas stream containing contaminants comprising:
   a first gas treatment member including a photocatalyst and a light source;
   a second gas treatment member including a plasma device, the first and second gas treatment members in fluid communication with each other and each of the first and second gas treatment members is configured to be selectively controllable between an on and an off condition; and
   a third gas treatment member including an adsorptive filter and a heater in fluid communication with the first and second gas treatment members, and the third gas treatment member being configured to selectively release contaminants based upon the off condition of the first gas treatment member.

2. The system as recited in claim 1, wherein the second gas treatment member is configured to be in the on condition generating a plasma in response to the first gas treatment member being in the off condition.

3. The system as recited in claim 2, wherein the third gas treatment member is configured to release contaminants in response to the heater providing heat and retain contaminants in response to the heater not providing heat.

4. The system as recited in claim 1, further including a cabinet enclosing the first, second and third gas treatment members.

5. The system as recited in claim 1, wherein the adsorptive filter includes a filter media selected from the group consisting of activated carbon, zeolite and combinations thereof.

6. The system as recited in claim 5, wherein the filter media includes a first layer of activated carbon and a second layer of zeolite located adjacent the first layer.

7. The system as recited in claim 1, wherein the plasma device is located downstream from the adsorptive filter.

8. The system as recited in claim 7, wherein the photocatalyst and light source are located downstream from the plasma device.

9. The system as recited in claim 8, further including an ozone-destroying material located between the plasma device and the photocatalyst.

10. The system as recited in claim 9, wherein the ozone-destroying material is a metal oxide disposed on a honeycomb structure.

11. A gas treatment system for treating a gas stream containing contaminants comprising:
    a first gas treatment member including a photocatalyst and a light source;
    a second gas treatment member including a plasma device; and
    a third gas treatment member including an adsorptive filter and a heater, the first, second and third gas treatment members in fluid communication with each other are configured to be selectively controllable between an on and an off condition and are configured to operate between a first mode and a second mode, in the first mode the first gas treatment member is in the on condition and the second and third gas treatment members are in the off condition, and in the second mode the first gas treatment member is in the off condition and the second and third gas treatment members are in the on condition.

12. The system as recited in claim 11, wherein the plasma device is located downstream from the adsorptive filter.

13. The system as recited in claim 12, wherein the photocatalyst is located downstream from the plasma device.

14. The system as recited in claim 13, further including an ozone-destroying material located between the plasma device and the photocatalyst.

15. The system as recited in claim 14, wherein the ozone-destroying material is a metal oxide disposed on a honeycomb structure.

* * * * *